(12) United States Patent
Mathieu

(10) Patent No.: US 7,109,386 B2
(45) Date of Patent: Sep. 19, 2006

(54) METHOD FOR PREPARING A HALOGENATED OLEFIN

(75) Inventor: Véronique Mathieu, Wavre (BE)

(73) Assignee: Solvay (Societe Anonyme), (BE)

( * ) Notice: Subject to any disclaimer, the term of this patent is extended or adjusted under 35 U.S.C. 154(b) by 0 days.

(21) Appl. No.: 10/472,784

(22) PCT Filed: Mar. 20, 2002

(86) PCT No.: PCT/EP02/03238

§ 371 (c)(1),
(2), (4) Date: Oct. 31, 2003

(87) PCT Pub. No.: WO02/076913

PCT Pub. Date: Oct. 3, 2002

(65) Prior Publication Data

US 2004/0116754 A1    Jun. 17, 2004

(30) Foreign Application Priority Data

Mar. 22, 2001 (FR) .................................. 01 03908

(51) Int. Cl.
*C07C 17/00* (2006.01)
*C07C 19/08* (2006.01)
*C07C 21/00* (2006.01)

(52) U.S. Cl. ...................... 570/161; 570/163; 570/164; 570/168; 570/172; 570/233; 570/235

(58) Field of Classification Search ................ 570/161, 570/163, 164, 168, 172, 233, 235
See application file for complete search history.

(56) References Cited

U.S. PATENT DOCUMENTS

| | | | | |
|---|---|---|---|---|
| 4,620,038 A | * | 10/1986 | Tanimoto et al. | 568/401 |
| 5,569,730 A | * | 10/1996 | Goodall et al. | 526/282 |
| 5,811,590 A | * | 9/1998 | Arnoldy et al. | 568/451 |
| 5,917,098 A | * | 6/1999 | Bertocchio et al. | 570/164 |
| 5,955,638 A | | 9/1999 | Schoebrechts et al. | |
| 6,080,888 A | * | 6/2000 | Wu et al. | 562/467 |

FOREIGN PATENT DOCUMENTS

EP    0905113    9/1999

* cited by examiner

*Primary Examiner*—Sikarl A. Witherspoon
(74) *Attorney, Agent, or Firm*—Connolly Bove Lodge & Hutz

(57) ABSTRACT

Process for the preparation of a halogenated olefin by reaction of an alkyne and/or of an allene compound with a hydrogen halide in a liquid medium comprising at least one hydrohalogenation catalyst comprising at least one palladium compound.

18 Claims, No Drawings

METHOD FOR PREPARING A HALOGENATED OLEFIN

Process for the preparation of a halogenated olefin

The present invention relates to a process for the preparation of a halogenated olefin, in particular 2-chloroprop-1-ene.

2-Chloroprop-1-ene is an intermediate in the synthesis of halogenated precursors of 1,1,1,3,3-pentafluorobutane (HFC-365 mfc) used as solvent and as blowing agent in the preparation of polymeric cellular foams. 2-Chloroprop-1-ene is particularly useful in the synthesis of the precursor 1,1,1,3,3-pentachlorobutane.

Patent Application EP-A-905 113 on behalf of the Applicant teaches a process for the preparation of 2-chloroprop-1-ene by reaction of methylacetylene and/or propadiene with hydrogen chloride in a liquid medium including at least
(a) one hydrochlorination catalyst which comprises at least one compound chosen from compounds of the metals from Group VIIIa and of the lanthanides; and
(b) one organic solvent capable of dissolving the catalyst.

Overall, this known process gives highly satisfactory results. However, it was desirable to find a process for the preparation of 2-chloroprop-1-ene by reaction of methylacetylene and/or of propadiene which makes it possible to obtain an improved selectivity for 2-chloroprop-1-ene. It was also desirable to find such a process which makes possible efficient conversion of methylacetylene and propadiene, providing even more efficient use of these starting materials.

The invention consequently relates to a process for the preparation of a halogenated olefin by reaction of an alkyne and/or of an allene compound with a hydrogen halide in a liquid medium comprising at least
(a) one hydrohalogenation catalyst comprising at least one palladium compound; and
(b) at least one organic solvent, chosen from organic nitrites, capable of dissolving the catalyst.

The alkynes of general formula (I)

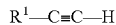

in which $R^1$ denotes a hydrogen, alkyl, aryl, carboxyl, ester or halogen group, are highly suitable as alkyne. Preferably, $R^1$ is chosen from a carboxyl group, an alkyl group comprising from 1 to 10 carbon atoms, a phenyl group optionally substituted by 1, 2 or 3 alkyl substituents comprising from 1 to 4 carbon atoms, an alkyl ester carrying an alkyl radical comprising from 1 to 10 carbon atoms, or an aryl ester.

The compounds of general formula (II)

$$R^2R^3C=C=CH_2 \qquad (II)$$

in which $R^2$ and $R^3$ independently denote a hydrogen, alkyl, aryl, carboxyl, ester or halogen group, are highly suitable as allene compound. Preferably, $R^2$ and $R^3$ are chosen independently from a hydrogen group, a carboxyl group, an alkyl group comprising from 1 to 10 carbon atoms, a phenyl group optionally substituted by 1, 2 or 3 alkyl substituents comprising from 1 to 4 carbon atoms, an alkyl ester carrying an alkyl radical comprising from 1 to 10 carbon atoms, or an aryl ester.

It has in fact been observed that the process according to the invention makes possible access, in a particularly selective way, to haloolefins of general formulae (III) and (IV)

$$R^1\text{---}XC=CH_2 \qquad (III)$$

$$R^2R^3C=XC\text{---}CH_3 \qquad (IV)$$

in which $R^1$, $R^2$ and $R^3$ have the same meaning as described above and X denotes a halogen preferably chosen from bromine and chlorine, in particular chlorine.

In the process according to the invention, it is preferable to employ a hydrogen halide chosen from hydrogen bromide and hydrogen chloride. Hydrogen chloride is particularly preferred.

The invention relates in particular to a process for the preparation of 2-chloroprop-1-ene by reaction of methylacetylene and/or of propadiene with hydrogen chloride in a liquid medium comprising at least
(a) one hydrochlorination catalyst comprising at least one compound chosen from palladium compounds; and
(b) at least one organic solvent, chosen from organic nitrites, capable of dissolving the catalyst.

It has been found, surprisingly, that the process according to the invention makes it possible to obtain 2-chloroprop-1-ene with an improved selectivity in comparison with the known process. Furthermore, the process according to the invention makes it possible to improve the conversion of methylacetylene while retaining a high selectivity for 2-chloroprop-1-ene. This makes it possible to increase the efficiency of the manufacture of 2-chloroprop-1-ene, in particular when a starting material comprising methylacetylene is employed.

The continuation of the description will relate in particular to the process for the synthesis of 2-chloroprop-1-ene. However, it is understood that the alternative forms and preferences described also apply, if appropriate, to the process according to the invention for the manufacture of a haloolefin of general formula (III) or (IV).

The process according to the invention advantageously takes place in the substantial absence of water.

An organic nitrile is used as solvent capable of dissolving the catalyst. The organic nitrile generally comprises 1, 2, 3 or 4 nitrile functionalities. Aliphatic nitrites of general formula $CH_3\text{---}(CH_2)_n\text{---}CN$ with n an integer from 3 to 7; aliphatic dinitriles of general formula $NC\text{---}(CH_2)_m\text{---}CN$ with m an integer from 3 to 10; and aromatic nitrites, such as benzonitrile and tolunitrile, can be used in particular. Aliphatic dinitriles of general formula $NC\text{---}(CH_2)_m\text{---}CN$ with m an integer from 3 to 10, preferably with m an integer from 4 to 6, are preferred. Adiponitrile is very particularly preferred.

The catalyst used in the process of the present invention comprises at least one palladium compound. The palladium compound is often chosen from complexes and salts comprising palladium in the 0 or 2 oxidation state. Preferably, use is made of a palladium compound comprising palladium in the 2 oxidation state. Advantageously, the palladium compounds employed are chosen from the halides. The chlorides or the bromides are preferred but any other compound which can be converted to halides in the presence of hydrogen halide can also be used. Palladium compounds complexed by electron-rich systems, such as amines, oxygen compounds, such as carbonyl compounds or ethers, which may be cyclic or -acyclic, sulphur compounds, aromatic compounds or compounds carrying aromatic rings, can also be employed. The salts formed between palladium and an acidic organic compound, not only with carboxylic acids but also with other compounds, such as acetylacetone, are advantageously regarded as usable palladium compounds. Palladium(0) complexes, such as the complexes formed with triphenylphosphine or triphenylphosphine oxide, can also be employed as catalyst. Palladium(II) complexes, such as π-allyl complexes, such as, for example, bis($\eta^3$-allyl-μ-chloropalladium(II)), can also be employed as catalyst.

Palladium(II) acetate, palladium(II) nitrate, palladium(II) bromide and palladium(II) chloride, for example, are suitable as palladium salts. Palladium(II) chloride and palladium(II) bromide are particularly preferred. Palladium(II) chloride is very particularly preferred.

Advantageously, the nature and/or the amount of catalyst employed is such that all the catalyst is in the dissolved form. However, it is also possible to employ a catalyst in an amount or of a nature such that a fraction at least of the latter is present in the liquid medium in the dispersed solid form, without prejudicing the invention. The amount of catalyst charged is generally greater than or equal to 0.1 millimol per litre of liquid medium. It is preferably greater than or equal to 0.5 millimol per litre of liquid medium. It is advantageously greater than or equal to 1 millimol per litre of liquid medium. The amount of catalyst is usually less than or equal to 50 millimol per litre of liquid medium. It is preferably less than or equal to 20 millimol per litre of liquid medium. It is advantageously less than or equal to 10 millimol per litre of liquid medium. Preferably, the liquid medium is composed essentially of an organic-nitrile-as-described-above.

The invention also relates to a catalytic system comprising any one of the abovementioned palladium compounds and any one of the abovementioned organic nitriles, preferably in the abovementioned amounts of catalyst in the organic nitrile.

In an alternative form of the process according to the invention, use is also made of a cocatalyst which comprises at least one compound of at least one metal from Groups Ib or IVb, such as copper, silver, tin or lead. There is a marked preference for metals such as copper and tin, in particular copper. Preferably, the compound of a metal from Groups Ib or IVb employed as cocatalyst in this embodiment is a chloride. Copper(II) chloride is particularly preferred. The cocatalyst is generally employed in a molar ratio with respect to the catalyst of greater than 0.1. This molar ratio is preferably greater than or equal to 1. This molar ratio is advantageously greater than or equal to 2. However, this molar ratio is usually less than 20. This molar ratio is preferably less than or equal to 15. This molar ratio is advantageously less than or equal to 10. The cocatalyst can be introduced at the beginning of the reaction, at the same time as the catalyst, or it can be introduced during the reaction.

In another alternative form, in addition to the palladium compound and the organic nitrile, the liquid medium comprises at least one organic cosolvent. The choice of the nature of the organic cosolvent employed is conditioned in particular by the need for it to be inert with regard to the reactants under the reaction conditions, for it to be miscible with the solvent at the reaction temperature and for it to be capable of dissolving it, in particular when the latter is solid at ambient temperature. Furthermore, for reasons of safety and of ease of use, organic cosolvents of low volatility are preferred. The choice of the organic cosolvent is also influenced by its ability to dissolve methylacetylene and/or propadiene. Cosolvents which satisfy the various criteria set out above are chosen from aliphatic, cycloaliphatic and aromatic hydrocarbons and their mixtures, for example paraffins comprising 7 to 15 carbon atoms and alkylbenzenes, in particular xylenes, propylbenzenes, butylbenzenes or methylethylbenzenes. The cosolvent employed is preferably chosen from commercial products composed of mixtures of aliphatic hydrocarbons, such as the product Isopar® from Esso or the product Shellsol® D70 from Shell, or of mixtures of aromatic compounds, such as the product Solvesso® from Esso or the product Shellsol® AB from Shell.

Appropriate cosolvents are, for example, saturated aliphatic cosolvents, such as the product Shellsol® D70, composed of petroleum fractions having a boiling point of greater than or equal to approximately 190° C. and less than or equal to approximately 250° C.

Other cosolvents which can be envisaged on the basis of the various criteria given above are some heavy halogenated compounds, such as haloalkanes, halobenzenes and other halogenated derivatives of aromatic compounds.

When the process according to the invention is carried out in the presence of a cosolvent, the ratio by weight of the organic nitrile to the cosolvent is generally at least 0.1. More often, this ratio is at least 0.2. It is preferably at least 0.3. If appropriate, when the process according to the invention is carried out in the presence of a cosolvent, the ratio by weight of the organic nitrile to the cosolvent is generally at most 10. More often, this ratio is at most 5. It is preferably at most 3.

In a preferred alternative form, the process according to the invention is carried out in the absence of cosolvent.

In the process according to the invention, a particularly preferred liquid medium comprises palladium(II) chloride as catalyst and adiponitrile as solvent. A liquid medium composed essentially of palladium(II) chloride as catalyst and of adiponitrile as solvent is more particularly preferred.

The process for the manufacture of 2-chloroprop-1-ene according to the invention is carried out by bringing methylacetylene and/or propadiene into contact with hydrogen chloride in any appropriate reactor including the liquid medium. This contacting operation is generally carried out by introducing a gas fraction comprising methylacetylene and/or propadiene into the liquid medium.

The introduction of the gas fraction into the liquid medium is preferably carried out so as to maximize the gas/liquid exchange surface area. Introduction and/or stirring means which provide good dispersion of the gas. in the form of bubbles in the liquid medium will preferably be chosen. Examples of introduction means are, inter alia, porous plates or porous sintered glasses exhibiting an appropriate porosity and distribution pipes exhibiting multiple holes allowing. the gas fraction to pass.

In the process according to the invention, the flow rate of the gases introduced to the reactor is advantageously adjusted so as to maximize the gas/liquid exchange surface area.

The process according to the invention can be carried out conventionally, batchwise or continuously, in any equipment promoting gas/liquid exchange, such as a plate column, a structured-packing -column, in particular a flooded structured-packing column, a reactor of saturator type or a bubble column. The term "reactor of saturator type" is understood to mean in particular a tubular reactor comprising, during the reaction, alternating segments of liquid medium and of gas which are propelled in the direction of the outlet of the tube by the pressure of the gas.

The devices employed in the process according to the invention are generally made of a material which exhibits sufficient resistance to corrosion in the presence of hydrogen chloride and of the liquid medium, in particular in the presence of the catalytic system. Materials which can be used are chosen, for example, from graphite impregnated with polymer and steels, for example of Hastelloy® and Inconel® type, optionally coated with polymer.

The polymer with which the graphite is impregnated or the steel is coated is preferably chosen from a fluoropolymer, in particular polytetrafluoroethylene (PTFE), and a phenolic polymer. Available examples of graphite impregnated with polymer are those sold under the names Graphilor®, which is a graphite impregnated with PTFE, and Diabon® NS-1, which is a graphite impregnated with phenolic polymer. An example of steel coated with polymer is that sold under the name Armilor, which is a steel coated with PTFE. The graphite impregnated with polymer or the coated steel is advantageously used to produce the parts of the reactor or other components of the equipment of. the process which are regularly in contact with the liquid medium, such as pumps or introduction means as described above.

Among the steels, steels of Hastelloy® B and C type are highly suitable. Steel of Hastelloy® C type is preferred. Steel of Hastelloy® C type is advantageously used to produce the parts of the reactor which are, if appropriate, substantially exclusively in contact with the gas phase present in the reactor.

The materials mentioned above are highly suitable for carrying out the process according to the invention. They can also be employed with other catalytic systems, such as disclosed, for example, in Application EP-A-905 113. The invention consequently also relates, in a specific aspect, to the use of reactors as described above comprising the materials as described above in carrying out a hydrochlorination reaction with hydrogen chloride in a-liquid medium including at least one hydrochlorination catalyst which preferably comprises at least one compound chosen from compounds of the metals from Group. VIIIa and of the lanthanides and one organic solvent capable of dissolving the catalyst.

In the process according to the invention, the gas/liquid contact time, which is the period during which the gas is in contact with the liquid medium, for example in the form of a bubble which passes through a given amount of liquid medium, is generally greater than or equal to 0.5 second. The contact time is advantageously greater than or equal to 1 second. The gas/liquid contact time generally does not exceed 5 minutes. It is generally less than or equal to 2 minutes. It is advantageously less than or equal to 1 minute. It has been found that particularly good selectivities for and yields of 2-chloroprop-1-ene are obtained by virtue of the use of the process according to the invention under the contact time conditions mentioned above.

In the process according to the invention, the molar ratio of the hydrogen chloride to the methylacetylene and/or propadiene introduced into the reactor is generally greater than or equal to approximately 0.5. This ratio is preferably greater than or equal to 1. This molar ratio is generally less than or equal to approximately 10. This ratio is preferably less than or equal to 5. Good results were obtained with a molar ratio of hydrogen chloride to the methylacetylene and/or propadiene introduced into the reactor of less than or equal to approximately 2.5. The methylacetylene and/or propadiene and the hydrogen chloride can be brought into contact in the reactor or can be mixed prior to their introduction into the reactor.

The process of the invention can be carried out from ambient temperature up to approximately 200° C. The catalyst has a tendency to decompose at a higher temperature. The preferred reaction temperature, that is to say that offering the best compromise between productive output, yield and stability of the catalyst, is greater than or equal to 80° C. The better results are obtained at temperatures of greater than or equal to approximately 100° C. The reaction temperature preferably does not exceed approximately 180° C. A reaction temperature of less than or equal to approximately 160° C. is particularly preferred.

The pressure is generally greater than or equal to atmospheric pressure and equal to or less than 15 bar. The pressure is preferably less than or equal to 10 bar. A pressure of less than or equal to 5 bar is particularly preferred. The process of the invention is often carried out at a pressure of close greater than or equal to 1 bar. A pressure of greater than or equal to 2 bar gives good results. A pressure of approximately 3 bar is particularly well suited. The flow rate of the reactants, generally gaseous reactants, is generally sufficient to make possible efficient mixing of the liquid medium. It is also possible to employ known means for stirring the liquid medium, such as mechanical stirrers.

In a continuous process, the residence time, which is the ratio of the volume of liquid medium in the reactor to the flow rate by volume of the reactants, is generally greater than or equal to 0.5 second. The residence time is advantageously greater than or equal to 1 second. The residence time generally does not exceed 5 minutes. It is generally less than or equal to 2 minutes. It is advantageously less than or equal to 1 minute.

In the process according to the invention, it is preferable to use, as reactant, a mixture of hydrocarbons comprising methylacetylene and propadiene, for example that sold by Air Liquide under the name of Tetrene®. Its molar composition is approximately 25% methylacetylene, 13% propadiene, 46% propylene, 4% propane and 12% $C_4$ hydrocarbons. Preferably, the liquid medium is saturated with hydrogen chloride before introducing the methylacetylene and/or propadiene into the reactor. This makes it possible to maintain a particularly good activity of the catalytic system during the reaction.

When a mixture of hydrocarbons comprising methylacetylene and propadiene is employed, it is particularly desirable to. achieve an efficient conversion of the methylacetylene and propadiene.

The invention consequently also relates to a method for the preparation of 2-chloroprop-1-ene by reaction of a methylacetylene/propadiene mixture with hydrogen chloride in a liquid medium comprising at least one hydrochlorination catalyst and at least one organic solvent capable of dissolving the catalyst, in which method
  (a) a methylacetylene/propadiene mixture is introduced into the liquid medium and
  (b) on conclusion of the reaction, 2-chloropropene is recovered, on the one hand, and a fraction comprising unreacted methylacetylene and unreacted propadiene is recovered, on the other hand, and
  (c) the fraction comprising unreacted methylacetylene and unreacted propadiene is recycled to Stage (a).

Preferably, the molar ratio of the methylacetylene to the propadiene in the fraction comprising unreacted methylacetylene and unreacted propadiene is substantially identical to the initial molar ratio between these same constituents. The variation in the molar ratio of the methylacetylene to the propadiene in the fraction comprising unreacted methylacetylene and unreacted propadiene in comparison with the initial molar ratio is generally less than or equal to 10%. This variation is preferably less than or equal to 5%. A variation of less than or equal to 1% is more particularly preferred. A variation of less than or equal to 0.5% is very particularly preferred. A variation of 0% can even be arrived at.

The variation can be adjusted, if necessary, by operations intended to alter the molar ratio of the methylacetylene to the propadiene, such as, for example, a contribution of one of these compounds or a selective separation operation, such as an adsorption. However, the process according to the invention described above makes it possible to obtain, on conclusion of the reaction, a fraction comprising unreacted methylacetylene and unreacted propadiene with a molar ratio of the methylacetylene to the propadiene which is substantially identical to the initial molar ratio.

The method according to the invention makes possible very efficient use of the starting materials while avoiding accumulation of one of the starting materials in the reactor.

The invention also relates to a process for the manufacture of a fluorinated compound, in particular a hydrofluoroalkane, comprising
 (a) the use of a halogenated olefin, in particular 2-chloroprop-1-ene, obtained according to the process according to the invention or according to the method according to the invention, in the manufacture of a halogenated precursor of the fluorinated compound,
 (b) the fluorination of the precursor obtained with a fluorinated reactant, preferably hydrogen fluoride, to form the fluorinated compound.

The manufacture of the halogenated precursor can, for example, be a telomerization reaction in which 2-chloroprop-1-ene is reacted with a haloalkane in the presence of a catalyst and optionally of a cocatalyst. This type of reaction is particularly well suited to the production of 1,1,1,3,3-pentachlorobutane, which is a halogenated precursor of 1,1,1,3,3-pentafluorobutane. In a preferred telomerization reaction, 2-chloroprop-1-ene is consequently reacted with tetrachloromethane in the presence of a catalyst comprising a copper compound and a cocatalyst chosen from amines to form 1,1,1,3,3-pentachlorobutane.

In the fluorination of the precursor obtained, the preferred fluorinated reactant is anhydrous hydrogen fluoride. The fluorination can be carried out in the presence or in the absence of fluorination catalyst. When the fluorination is carried out in the presence of a catalyst, the latter is advantageously chosen from the halides of metals from Groups 4, 5, 14 and 15, in particular tin, antimony, titanium, niobium and tantalum derivatives. The preferred hydrofluoroalkane is 1,1,1,3,3-pentafluorobutane.

The invention is illustrated without implied limitation in the following examples.

EXAMPLE 1

The reaction was carried out in a reactor of saturator type equipped with a jacket in which oil thermostatically controlled at the temperature of the test circulates and surmounted by a cooled reflux condenser in order to condense the solvent and cosolvent vapours. 0.15 mmol of $PdCl_2$ were dissolved in 80 ml of adiponitrile in a beaker by gently heating. After the palladium chloride had completely dissolved, the liquid phase was poured into the reactor, heated beforehand to 140° C. Hydrogen chloride was then injected at a flow rate of 1.3 l/h for 30 minutes. Subsequently, in conjunction with the hydrogen chloride, a mixture composed, on a molar basis, of 25% methylacetylene, 13% propadiene, 46% propylene, 4% propane and 12% $C_4$ hydrocarbons was injected into the reactor at a flow rate of 2.4 l/h. The residence time in the reactor was 23 s.

The reaction products obtained over time were analysed by an in-line gas-phase chromatographic analysis. The results are presented in Table 1 below. In this table, the degree of conversion is the ratio of the initial concentration of methylacetylene and propadiene decreased by its final concentration divided through the initial concentration, multiplied by 100; the selectivity for 2-chloroprop-1-ene is the ratio of the final concentration of 2-chloroprop-1-ene divided through the initial concentration of methylacetylene and propadiene decreased by its final concentration, multiplied by 100.

EXAMPLE 2 (COMPARISON)

A liquid medium comprising 0.15 mmol of $PtCl_2$ in 80 ml of adiponitrile was employed. The reaction was carried out in the same equipment and under the same conditions as in Example 1, except for the residence time, which was brought to 46 s. The result obtained is shown in Table 1.

TABLE 1

| Example (No.) | Conversion of propadiene (%) | Conversion of methylacetylene (%) | Selectivity for 2-chloroprop-1-ene (%) |
|---|---|---|---|
| 1 | 85 | 85 | 94.5 |
| 2 (comp.) | 79 | 46 | 85 |

It is apparent that the process according to the invention makes it possible to obtain 2-chloroprop-1-ene with a better selectivity in comparison with the process catalysed by $PtCl_2$/adiponitrile. The conversion of methylacetylene is greatly improved. The process according to the invention thus provides unexpected results which are better in comparison with the process catalysed by $PtCl_2$/adiponitrile. The degrees of conversion of propadiene and of methylacetylene are identical. Consequently, the mixture of unconverted propadiene and unconverted methylacetylene is, after separation of the 2-chloroprop-1-ene, suitable for recycling to the manufacturing reaction.

The invention claimed is:

1. A process for the preparation of a halogenated olefin by reaction of an alkyne and/or of an allene compound with a hydrogen halide in a liquid medium comprising at least
 (a) one hydrohalogenation catalyst comprising at least one palladium compound; and
 (b) at least one organic solvent, chosen from organic nitriles, capable of dissolving the catalyst.

2. The process according to claim 1, in which the alkyne corresponds to the general formula (I)

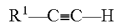

in which $R^1$ denotes an alkyl, aryl, carboxyl, ester or halogen group, and/or the allene compound corresponds to the general formula (II)

$$R^2R^3C=C=CH_2 \qquad (II)$$

in which $R^2$ and $R^3$ independently denote a hydrogen, alkyl, aryl, carboxyl, ester or halogen group.

3. The process according to claim 1, in which 2-chloroprop-1-ene is prepared by reaction of methylacetylene and/or propadiene with hydrogen chloride.

4. The process according to claim 1, in which the palladium compound is chosen from complexes and salts comprising palladium in the 0 or 2 oxidation state.

5. The process according to claim 4, in which the palladium compound comprises palladium in the 2 oxidation state.

6. The process according to claim 5, in which the palladium compound is a salt chosen from palladium (II) acetate, palladium (II) nitrate, palladium (II) bromide or palladium (II) chloride.

7. The process according to claim 6, in which the palladium compound is palladium (II) chloride.

8. The process according to claim 1, in which the organic nitrile comprises 1,2,3 or 4 nitrile functionalities.

9. The process according to claim 8, in which the organic nitrile is adiponitrile.

10. The process according to claim 1, in which the pressure at which the reaction is carried out is from 1 to 5 bar and the temperature at which the reaction is carried out is from 100 to 160° C.

11. A Method for the preparation of 2-chloroprop-1-ene by reaction of a methylacetylene/propadiene mixture with hydrogen chloride in a liquid medium comprising at least one hydrochlorination catalyst comprising and at least one palladium compound, and at least one organic solvent chosen from organic nitriles, capable of dissolving the catalyst, in which method has the following stages:
   (a) a methylacetylene/propadiene mixture is introduced into the liquid medium and
   (b) on conclusion of the reaction, 2-chloropropene is recovered, on the one hand, and a fraction comprising unreacted methylacetylene and unreacted propadiene is recovered, on the other hand, and
   (c) the fraction comprising unreacted methylacetylene and unreacted propadiene is recycled to stage (a) and wherein the molar ratio of methylacetylene to propadiene in the fraction comprising unreacted methylacetylene and unreacted propadiene is substantially identical to the initial molar ratio between these same constituents.

12. A process for the manufacture of a fluorinated compound, comprising
   (a) preparing a halogenated precursor with the halogenated olefin, obtained by reacting an alkyne and/or of an allene compound with a hydrogen halide in a liquid medium comprising at least
   (a) one hydrohalogenation catalyst comprising at least one palladium compound; and
   (b) at least one organic solvent, chosen from organic nitriles, capable of dissolving the catalyst,
   (b) fluorinating the precursor obtained with a fluorinated reactant to form the fluorinated compound.

13. The process according to claim 12, in which the fluorinated compound is 1,1,1,3,3-penta-fluorobutane.

14. The process according to claim 12, wherein said halogenated olefin is 2-chloroprop-1-ene and said fluorinated reactant is hydrogen fluoride.

15. The process for the manufacture of a fluorinated compound comprising
   (a) preparing a halogenated precursor with the halogenated olefin, obtained according to the method of claim 11 (b) fluorinating the precursor obtained with a fluorinated reactant, to form the fluorinated compound.

16. The process according to claim 1, wherein said halogenated olefin corresponds to the formula (III) or (IV)

$$R^1\text{—XC}=CH_2 \quad (III)$$

$$R^2R^3C=XC\text{—}CH_3 \quad (IV)$$

$R^1$ denotes an ailcyl, aryl, carboxyl, ester or halogen group, $R^2$ and $R^3$ independently denote a hydrogen, alkyl, aryl, carboxyl, ester or halogen group X is a halogen.

17. The process according to claim 1, wherein said hydrogen halide is hydrogen chloride.

18. The process according to claim 15, in which the alkyne corresponds to the general formula (I)

$$R^1\text{—C}\equiv C\text{—H}$$

in which $R^1$ denotes an alkyl, aryl, carboxyl, ester or halogen group, and/or the allene compound corresponds to the general formula (II)

$$R^2R^3C=C=CH_2 \quad (II)$$

in which $R^2$ and $R^3$ independently denote a hydrogen, alkyl, aryl, carboxyl, ester or halogen group.

* * * * *

UNITED STATES PATENT AND TRADEMARK OFFICE
CERTIFICATE OF CORRECTION

| | | |
|---|---|---|
| PATENT NO. | : 7,109,386 B2 | Page 1 of 1 |
| APPLICATION NO. | : 10/472784 | |
| DATED | : September 19, 2006 | |
| INVENTOR(S) | : Véronique Mathieu | |

It is certified that error appears in the above-identified patent and that said Letters Patent is hereby corrected as shown below:

Column 9, line 9, "11. A Method for the preparation of 2-cloroprop-l-ene" should read -- 11. A method for the preparation of 2-cloroprop-l-ene --

Column 10, line 20, "$R^1$ denotes an ailcyl, aryl, carboxyl, ester or halogen" should read -- $R^1$ denotes an alkyl, aryl, carboxyl, ester or halogen --

Signed and Sealed this

Sixteenth Day of January, 2007

JON W. DUDAS
*Director of the United States Patent and Trademark Office*